(12) United States Patent
Zhang et al.

(10) Patent No.: US 10,332,811 B2
(45) Date of Patent: Jun. 25, 2019

(54) FILM TEST STRUCTURE AND ARRAY SUBSTRATE

(71) Applicants: BOE TECHNOLOGY GROUP CO., LTD., Beijing (CN); HEFEI XINSHENG OPTOELECTRONICS TECHNOLOGY CO., LTD., Hefei, Anhui (CN)

(72) Inventors: Miao Zhang, Beijing (CN); Jing Sun, Beijing (CN); Wuxia Fu, Beijing (CN)

(73) Assignees: BOE TECHNOLOGY GROUP CO., LTD., Beijing (CN); HEFEI XINSHENG OPTOELECTRONICS TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 15/573,067

(22) PCT Filed: May 5, 2017

(86) PCT No.: PCT/CN2017/083195
§ 371 (c)(1),
(2) Date: Nov. 9, 2017

(87) PCT Pub. No.: WO2018/036200
PCT Pub. Date: Mar. 1, 2018

(65) Prior Publication Data
US 2018/0358273 A1   Dec. 13, 2018

(30) Foreign Application Priority Data

Aug. 26, 2016   (CN) .......................... 2016 2 0956579

(51) Int. Cl.
*G01R 31/28*   (2006.01)
*H01L 21/66*   (2006.01)
(Continued)

(52) U.S. Cl.
CPC .......... *H01L 22/32* (2013.01); *G01R 31/2886* (2013.01); *H01L 22/14* (2013.01);
(Continued)

(58) Field of Classification Search
CPC ..... G01R 31/2886; H01L 22/14; H01L 22/32; H01L 27/124
See application file for complete search history.

(56) References Cited

U.S. PATENT DOCUMENTS 5,051,690 A * 9/1991 Maly ...................... G01R 27/14
257/48
5,514,974 A * 5/1996 Bouldin .................. H01L 22/34
324/750.3
(Continued)

FOREIGN PATENT DOCUMENTS

CN        202166811 U    3/2012
CN        103217459 A    7/2013
(Continued)

OTHER PUBLICATIONS

International Search Report and Written Opinion dated Jun. 30, 2017; PCT/CN2017/083195.

*Primary Examiner* — Allan R Wilson
(74) *Attorney, Agent, or Firm* — Ladas & Parry LLP

(57) ABSTRACT

A film test structure and an array substrate are provided. The film test structure includes a conductive film to be tested; a plurality of test leads arranged at a different layer from the conductive film to be tested and electrically connected with the conductive film to be tested respectively; and a plurality of test terminals electrically connected with the plurality of test leads respectively.

20 Claims, 4 Drawing Sheets

(51) Int. Cl.
*H01L 23/544* (2006.01)
*H01L 27/12* (2006.01)

(52) U.S. Cl.
CPC ............ *H01L 23/544* (2013.01); *H01L 27/12* (2013.01); *H01L 27/124* (2013.01)

(56) References Cited

U.S. PATENT DOCUMENTS

| | | | | |
|---|---|---|---|---|
| 5,917,197 A * | 6/1999 | Alswede | ................. | H01L 22/32 257/203 |
| 6,842,028 B2 * | 1/2005 | Song | ................... | G01R 31/2853 324/537 |
| 2004/0155316 A1 * | 8/2004 | Saito | ........................ | H01L 22/34 257/536 |
| 2006/0109022 A1 * | 5/2006 | Yoshida | ............. | G01R 31/2853 324/750.03 |
| 2008/0160656 A1 * | 7/2008 | Chanda | .............. | G01R 31/2858 438/17 |
| 2014/0329342 A1 | 11/2014 | Zeng | | |
| 2018/0083051 A1 * | 3/2018 | Chan | ....................... | H01L 21/77 |

FOREIGN PATENT DOCUMENTS

| | | |
|---|---|---|
| CN | 203217210 U | 9/2013 |
| CN | 103811469 A | 5/2014 |
| CN | 104133333 A | 11/2014 |
| CN | 205959980 U | 2/2017 |
| JP | 2007-072325 A | 3/2007 |

* cited by examiner

FILM TEST STRUCTURE AND ARRAY SUBSTRATE

TECHNICAL FIELD

Embodiments of the present disclosure relate to a film test structure and an array substrate.

BACKGROUND

In a field of display technology, for example, in a liquid crystal display or an organic electroluminescent display device, a thin film transistor is a basic component of an array substrate. The characteristics of the films of the thin film transistor affect the electrical performance of the thin film transistor, and thus affect the final display effect of the display devices.

Square resistance is an important means of evaluating film properties. At present, square resistance is usually measured by a four-probe method. Tests are performed by means of four probes with equidistant and aligned in a straight line, and the four probes are in contact with the film to be tested directly. For example, FIG. 1 is a schematic diagram for testing square resistance. The detector comprises four probes, and distances between any adjacent probes are equal. In a case that the probes are pressed on a conductive film material, the square resistance of the material is illustrated by the resistance meter, and the principle is that the two probes at two outer ends produce a current field and the two probes at the inner side test a potential difference formed by the current field on the two inner probes. The larger the resistance is, the greater the potential difference is, so that the square resistance of the film to be tested is measured.

SUMMARY

At least one embodiment of the present disclosure provides a film test structure, and the film test structure comprises: a conductive film to be tested; a plurality of test leads, arranged at a different layer from the conductive film to be tested and electrically connected with the conductive film to be tested respectively; and a plurality of test terminals, electrically connected with the plurality of test leads respectively.

For example, in the film test structure provided by at least one embodiment of the present disclosure, one end of each of the test leads is connected with the conductive film to be tested and the other end of the each of the test leads is connected with one of the test terminals.

For example, in the film test structure provided by at least one embodiment of the present disclosure, the plurality of test leads are formed integrally with the plurality of test terminals respectively.

For example, in the film test structure provided by at least one embodiment of the present disclosure, the test leads are disposed above or below the conductive film to be tested.

For example, the film test structure provided by at least one embodiment of the present disclosure further comprises an insulating layer, the insulating layer is disposed between the conductive film to be tested and the test terminals, the insulating layer is provided with a plurality of first via holes, and the plurality of test leads are electrically connected with the conductive film to be tested by the corresponding first via holes respectively.

For example, in the film test structure provided by at least one embodiment of the present disclosure, the first via holes are arranged in an intermediate region of the conductive film to be tested.

For example, in the film test structure provided by at least one embodiment of the present disclosure, distances between any adjacent first via holes are approximately equal.

For example, in the film test structure provided by at least one embodiment of the present disclosure, the plurality of first via holes are aligned in a straight line.

For example, in the film test structure provided by at least one embodiment of the present disclosure, a number of the first via holes is four, and the four first via holes are arranged in an equilateral quadrilateral.

For example, in the film test structure provided by at least one embodiment of the present disclosure, the plurality of test terminals and the conductive film to be tested are arranged in a same layer and isolated from each other, or the plurality of test terminals and the plurality of test leads are arranged in a same layer and electrically connected with each other.

For example, in the film test structure provided by at least one embodiment of the present disclosure, in a case that the plurality of test terminals and the conductive film to be tested are arranged in a same layer, the insulating layer is further provided with a plurality of second via holes, and the plurality of test terminals are electrically connected with the plurality of the test leads by the second via holes respectively.

At least one embodiment of the present disclosure further provides an array substrate, and the array substrate comprises the film test structure described above, the conductive film to be tested is a gate film, a source and drain electrode film, or a pixel electrode film.

For example, in the array substrate provided by at least one embodiment of the present disclosure, in a case that the conductive film to be tested is the gate film, the plurality of test leads are located at a same layer as the source and drain electrode film, and the plurality of test terminals are located at a same layer as the gate film or located at a same layer as the source and drain electrode film.

For example, in the array substrate provided by at least one embodiment of the present disclosure, in a case that the conductive film to be tested is the source and drain electrode film, the plurality of test leads are located at a same layer as the gate film, and the plurality of test terminals are located at a same layer as the gate film layer or located at a same layer as the source and drain electrode film.

For example, in the array substrate provided by at least one embodiment of the present disclosure, in a case that the conductive film to be tested is the pixel electrode film, the plurality of test leads are located at a same layer as the source and drain electrode film, and the plurality of test terminals are located at a same layer as the pixel electrode film or located at a same layer as the source and drain electrode film.

BRIEF DESCRIPTION OF THE DRAWINGS

In order to clearly illustrate the technical solution of the embodiments of the disclosure, the drawings of the embodiments will be briefly described in the following, it is obvious that the described drawings are only related to some embodiments of the disclosure and thus are not limitative of the disclosure.

DETAILED DESCRIPTION

In order to make objects, technical details and advantages of the embodiments of the present disclosure apparent, the technical solutions of the embodiments will be described in a clearly and fully understandable way in connection with the drawings related to the embodiments of the disclosure. It is obvious that the described embodiments are just a part but not all of the embodiments of the disclosure. Based on the described embodiments herein, those skilled in the art can obtain other embodiment(s), without any inventive work, which should be within the scope of the disclosure.

Unless otherwise defined, the technical terms or scientific terms used herein have the same meanings as commonly understood by one of ordinary skill in the art to which the present invention belongs. The terms "first," "second," etc., which are used in the description and the claims of the present application for invention, are not intended to indicate any sequence, amount or importance, but distinguish various components. The terms "comprises," "comprising," "includes," "including," etc., are intended to specify that the elements or the objects stated before these terms encompass the elements or the objects and equivalents thereof listed after these terms, but do not preclude the other elements or objects. The phrases "connect", "connected", etc., are not intended to define a physical connection or mechanical connection, but may include an electrical connection, directly or indirectly. "Over," "under," "right," "left" and the like are only used to indicate relative position relationship, and when the position of the object which is described is changed, the relative position relationship may be changed accordingly.

Square resistance is usually measured by a four-probe method, and a test is performed by four probes with equidistant and aligned in a straight line. For a conductive film, square resistance is only related to a thickness of the conductive film to be tested. Square resistance is defined as: $R\square=\rho/t$, and $\rho$ is metal resistivity and t is the thickness of the conductive film to be tested.

The test requirement of square resistance includes: a distance from any probe to a boundary of the conductive film to be tested should much larger than a distance between any adjacent probes. For example, the distance from each probe to the boundary of the conductive film to be tested is at least 10 times greater than the distance between any adjacent probes; and the probes need to be placed at equal intervals.

In a case that four probes with equidistant and aligned in a straight line to measure square resistance, square resistance is calculated by the following formula:

$$\rho = 2\pi \cdot S_{probe} \frac{U_{23}}{I_{14}}$$ Formula (1)

Figure 1:
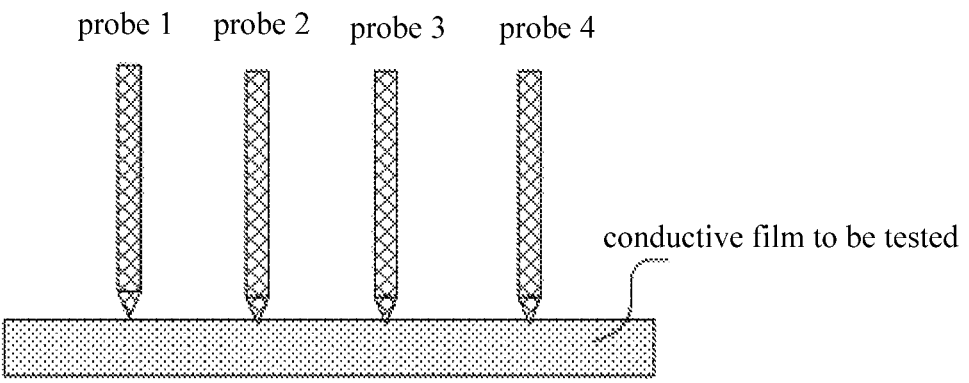
FIG. 1 is a schematic diagram for testing square resistance.

As illustrated in FIG. 1, the probe 1, the probe 2, the probe 3 and the probe 4 are arranged on the conductive film to be tested, $S_{probe}$ refers to a distance between adjacent probes, $U_{23}$ is a voltage difference between the probe 2 and the probe 3, and $I_{14}$ is a current between the probe 1 and the probe 4.

Figure 2:
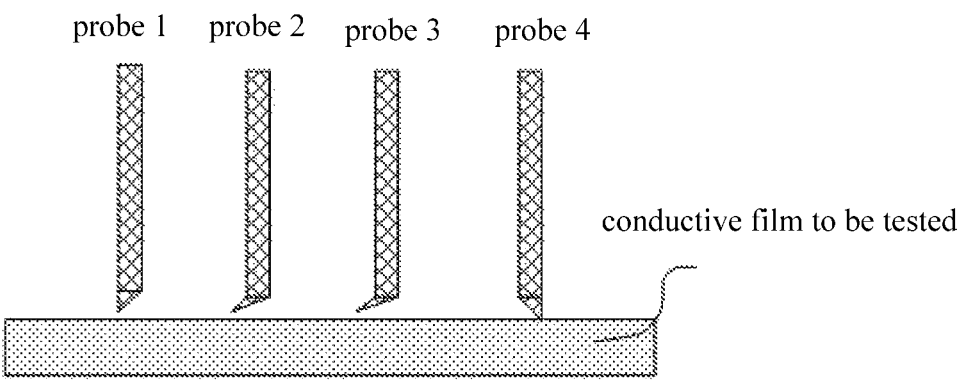
FIG. 2 is a schematic diagram of the probes in FIG. 1 after deformation.

In a conventional process of manufacturing the array substrate, for example, metal films or transparent conductive films are needed to be formed to form circuit structures such as gate lines, data lines, and pixel electrodes. In order to detect the film qualities of these conductive films, it is possible to measure the square resistances of these conductive films. The square resistance is measured after the conductive film to be tested is formed and before the etching operation, and in the process of testing, the probes are placed in a region to be etched to avoid the damage to the film. The inventors of the present disclosure note that, in a case that the probes have been used for a long time the probes will be damaged such as bending, offset and so on, which results in the change of the distance between the adjacent probes and further leads to measurement errors. Therefore, the resistance calculated by the above formula (1) is inaccurate, the test accuracy is degraded, and thus it is necessary to change the probes frequently. For example, FIG. 2 is a schematic diagram of the probes after deformation. As illustrated in FIG. 2, the probes are bent and deformed, which results in the change of the distance of the adjacent probes, and an error is occurred in a case that square resistance is calculated by the above formula (1). Moreover, the inventors find that it is possible to perform a test collectively after the formation of the films and the formation of the square resistance test pattern, so that it is more convenient to operate.

For example, in order to solve the problem of inaccurate measurement of square resistance due to the change of the distance of the adjacent probes, which caused by the bending deformation of the probes with a long term use. At least one embodiment of the present disclosure provides a film test structure, and the film test structure comprises: a conductive film to be tested; a plurality of test leads, arranged at a different layer from the conductive film to be tested and electrically connected with the conductive film to be tested respectively; and a plurality of test terminals, electrically connected with the plurality of test leads respectively.

Figure 3:
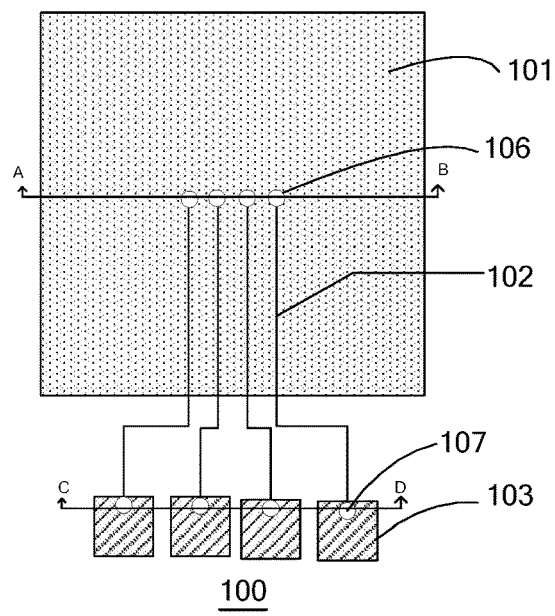
FIG. 3 is a schematic diagram of a film test structure provided by an embodiment of the present disclosure.

At least one embodiment of the present disclosure provides a film test structure, and FIG. 3 is a schematic diagram of a film test structure provided by an embodiment of the present disclosure. As illustrated in FIG. 3, the film test structure 100 comprises a conductive film to be tested 101, a plurality of test leads 102, and a plurality of test terminals 103. The plurality of test leads 102 are arranged at a different layer from the conductive film to be tested, and electrically connected with the conductive film to be tested 101 respectively; and the plurality of test terminals 103 are electrically connected with the plurality of test leads 102 respectively.

It should be noted that, the plurality of test leads 102 are arranged at a different layer from the conductive film to be tested means that the plurality of test leads 102 are formed in a film forming process different from a film forming process of the conductive film to be tested 101, and the plurality of test leads 102 are not a portion of the conductive film to be tested 101.

As illustrated in FIG. 3, test points on the conductive film to be tested 101 are led out of the conductive film to be tested 101 by the plurality of test leads 102, and the test points on the conductive film to be tested 101 is replaced by the plurality of test terminals 103. In this way, as long as the probes move in the corresponding test terminals 103, the measured resistance is substantially the resistance at the respective test points electrically connected with the respective test terminals 103.

In a case that the film test structure in at least one embodiment of the present disclosure is adopted, and in a case that the bending deformation of the probe(s) is caused by a long term use and the distance between the adjacent probes is changed, as long as each of the probes moves in the corresponding test terminal 103, the measured square resistance is still accurate, that is, it is convenient to test square resistance by using the film test structure provided by the embodiment of the present disclosure, and the test accuracy is guaranteed to avoid the frequent replacement of the probes, thereby the production cost is reduced.

For example, as illustrated in FIG. 3, the plurality of test leads 102 in the film test structure 100 are disposed above or below the conductive film to be tested 101.

For example, the film test structure 100 is formed in a blank region of a substrate. Pixel regions for at least one display panel are formed on the substrate, and the blank region is distributed around or between the pixel regions. The blank region is removed after the substrate is cut.

For example, the conductive film to be tested 101 is a pixel electrode film or a common electrode film made of a transparent conductive oxide, a gate film, or a source and drain electrode film.

For example, the manufacturing process of the conductive film to be tested comprises: depositing a conductive film on the substrate by means of magnetron sputtering or vapor deposition (for example, chemical vapor deposition), and photoresist is coated on the conductive film, and then processes of exposure, development, etching and stripping off the photoresist are performed to form the conductive film to be tested 101 and circuit structures (for example, gate lines, gate electrodes, data lines, source and drain electrodes, pixel electrodes, common electrodes, etc.) formed in the pixel regions correspondingly.

The following illustration is conducted by taking the gate metal film as the conductive film to be tested as an example, the test leads 102 are formed when the source and drain electrode film, or the pixel electrode film is formed, so that no additional process operation is needed. For example, the process of forming the test leads comprises: depositing a source and drain metal film in a magnetron sputtering method and so on, and photoresist is coated on the conductive film, and then the processes of exposure, development, etching and stripping off the photoresist are performed to form the test leads 102 on the substrate. Likewise, if the conductive film to be tested is a source and drain metal film, the test leads may be formed in a same layer as the gate metal film or the pixel electrode film.

For example, as illustrated in FIG. 3, the plurality of test terminals 103 and the conductive film to be tested 101 are arranged in a same layer and isolated from each other, or the plurality of test terminals 103 and the plurality of test leads 102 are arranged in a same layer and electrically connected with each other. So that the separate process of preparing the test terminals is saved. By taking the case in which the test terminals 103 and the conductive film to be tested 101 are arranged in a same layer and isolated from each other as an example, the test terminals and the conductive film to be tested are formed at the same time.

For example, as illustrated in FIG. 3, a width of each of the test terminals 103 is greater than a width of the corresponding test lead 102, and a size of each of the test terminals 103 should be appropriate for the measurement of the probes, and a shape of each of the test terminals 103 is not limited, as long as it is appropriate for the measurement of the probes. As illustrated in FIG. 3, the test terminal 103 is in a shape of square, and in other embodiments of the present disclosure, the shape of the test terminal 103 may be a circular, a rectangular, or a polygonal, and so on.

For example, under the premise that the test terminals are insulated from the conductive film to be tested, the test terminals may be arranged at any positions around the conductive film to be tested; in order to ensure the convenience of testing, the test terminals are arranged in a straight line. In a case that the width of the each test lead is fixed, the length of each test lead is arranged to the shortest to reduce the influence of the resistance of the test lead by itself on the accuracy of the test result, and to ensure that the test leads can lead the test points out of the conductive film to be tested.

Figure 4A:
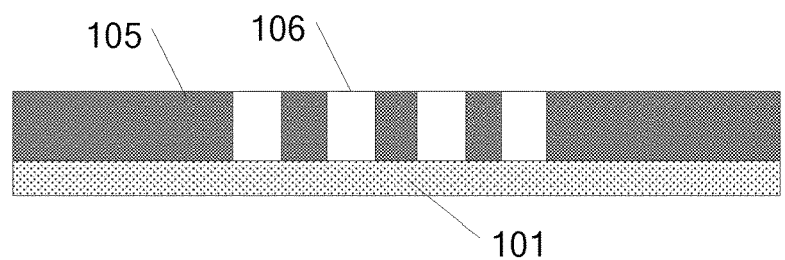
FIG. 4a is a schematic diagram of a cross sectional structure of the film test structure in FIG. 3 taken along line A-B.

For example, FIG. 4a is a schematic diagram of a cross sectional structure of the film test structure in FIG. 3 taken along line A-B, as illustrated in FIG. 4a, the film test structure further comprises an insulating layer 105 arranged at one side of the conductive film to be tested 101, the insulating layer 105 is provided with a plurality of first via holes 106, and the plurality of test leads are electrically connected with the conductive film to be tested 101 by the corresponding first via holes 106 respectively.

For example, as illustrated in FIG. 4a, the first via holes 106 are arranged in an intermediate region of the conductive film to be tested 101. For example, the geometry defined by the plurality of first via holes 106 passes through or covers the center of the conductive film to be tested 101. For example, the case that the plurality of first via holes 106 are aligned in a straight line means that the center of the conductive film to be tested 101 is located at the straight line along which the first via holes 106 are arranged; the case that the plurality of first via holes 106 are arranged in a polygonal shape means that the center of the conductive film to be tested 101 is located at the polygonal shape formed by the plurality of first via holes 106.

For example, as illustrated in FIG. 4a, the distances between any adjacent first via holes are approximately equal.

For example, as illustrated in FIG. 4a, the number of the first via holes is four, and the four first via holes 106 are aligned in a straight line.

Figure 5:
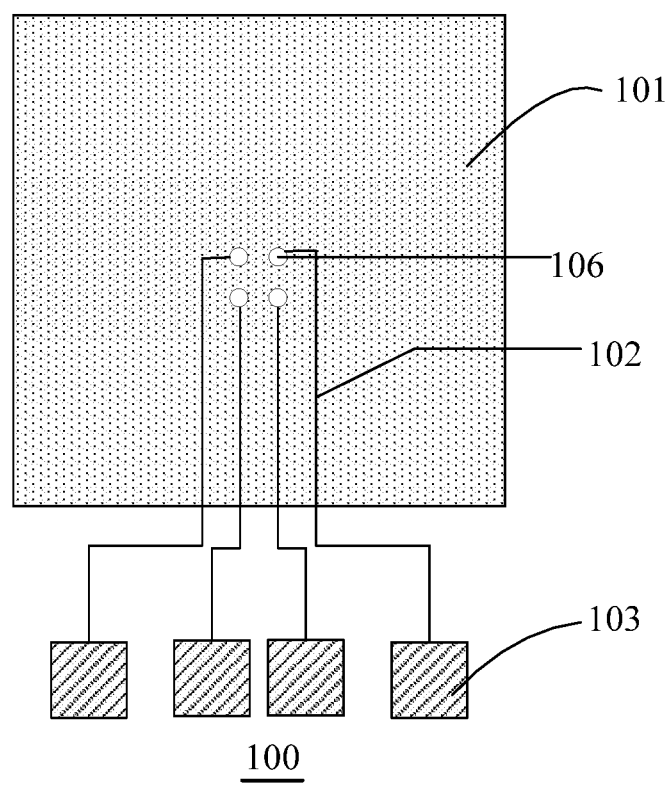
FIG. 5 is a schematic diagram of another film test structure provided by an embodiment of the present disclosure.

For example, as illustrated in FIG. 5, the four first via holes are arranged in a shape of a square or a diamond, as long as the distances between the adjacent first via holes are approximately equal. In a case that the four first via holes are arranged in a shape of a square or a diamond, the formula used for calculating the resistance should be multiplied by a corresponding coefficient.

Figure 4B:
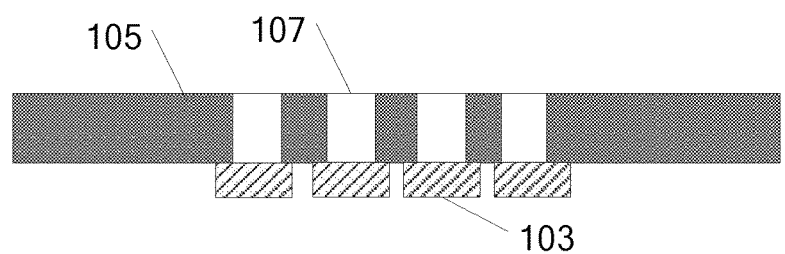
FIG. 4b is a schematic diagram of a cross sectional structure of the film test structure in FIG. 3 taken along line C-D.

For example, FIG. 4b is a schematic diagram of a cross sectional structure of the film test structure in FIG. 3 taken along line C-D, the number of the first vias is four, and the four first vias are aligned in a straight line.

FIG. 4b is a schematic view of the sectional structure of the film test structure in FIG. 3, which is cut along line C-D, as illustrated in FIG. 3 and FIG. 4b, in a case that the plurality of test terminals are located at a same layer as the conductive film to be tested, the insulating layer 105 further comprises a plurality of second via holes 107, the plurality of test terminals 103 are electrically connected with the plurality of test leads 102 by the corresponding second via holes 107 respectively.

It should be noted that, the case that the plurality of test leads are arranged at a same layer as the conductive film to be tested means that the plurality of test leads 102 are formed in a same film forming process as the conductive film to be tested 101.

After the film test structure in the embodiment of the present disclosure is manufactured, a group of four probes contact the four terminals. An electrical current is input to the probe at one end and the current is output from the probe at another end, and at the same time the voltage difference between the two terminals in the middle is measured, and square resistance is calculated by the square resistance formula. In a case that the square resistance test is performed on the film test structure provided by an embodiment of the present disclosure, the contact position of the probe is on the test terminal; even if the probe has been deformed for long time use, because of the large area of the test terminal, the test results will not be changed due to the variation of the distance of adjacent probes, and an error will not be occurred when square resistance is tested.

For example, in an embodiment of the present disclosure, the arrangement of the plurality of via holes is not limited to a straight line and an equilateral quadrilateral, other arrangement shapes are also be applicable, as long as the arrangement shapes match the corresponding calculation formulas for square resistance, and detailed descriptions will be omitted herein.

Figure 6:
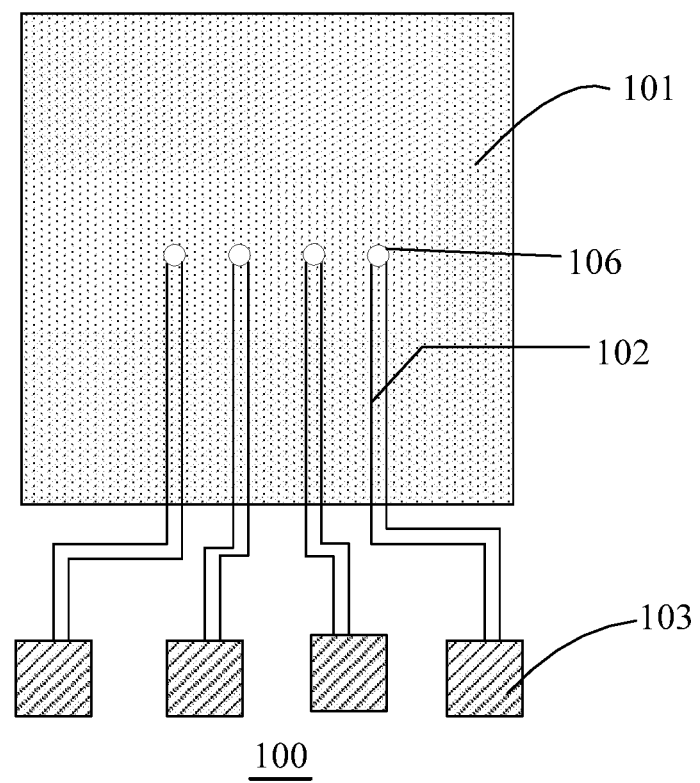
FIG. 6 is a schematic diagram of another film test structure provided by an embodiment of the present disclosure.

At least one embodiment of the present disclosure further provides another film test structure, and FIG. 6 is a schematic diagram of a film test structure provided by an embodiment of the present disclosure, in the film test structure, the ends of the plurality of test leads 102 extend out of the corresponding test terminals 103, and the test leads 102 and the test terminals 103 are formed integrally.

For example, the plurality of test terminals 103 are formed by extending the ends of the plurality of test leads 102, and the width of each of the test terminals 103 is larger than the width of each of the corresponding test leads 102, and the plurality of test leads 102 and the plurality of test terminals 103 are located in a same layer. As illustrated in FIG. 6, the test terminals 103 are formed by extending the ends of the plurality of test leads 102. For example, the planar shape of each test terminal 103 is a square and the side length of the square is greater than the width of the test lead 102.

In at least one embodiment of the present disclosure, other structural features may be referred to those described above in addition to the feature that the plurality of test terminals 103 are formed by extending the ends of the plurality of test leads 102, and detailed descriptions will be omitted herein.

For example, in the embodiment of the present disclosure, the arrangement of the plurality of via holes is not limited to a straight line and an equilateral quadrilateral, other arrangement shapes are also applicable, as long as the arrangement shapes match the corresponding calculation formulas for square resistance, and detailed descriptions will be omitted herein.

At least one embodiment of the present disclosure further provides an array substrate, and the array substrate comprises any one of the above-mentioned film test structures.

For example, the conductive film to be tested is a gate film, a source and drain electrode film, or a pixel electrode film.

For example, in a case that the conductive film to be tested is the gate film, the plurality of test leads are located at a same layer as the source and drain electrode film, and the plurality of test terminals are located at a same layer as the gate film or located at a same layer as the source and drain electrode film. If the film test structure as illustrated in FIG. 6 is used, the plurality of test terminals are located at the same layer as the plurality of test leads.

For example, in a case that the conductive film to be tested is the source and drain electrode film, the plurality of test leads are located at a same layer as the gate film, and the plurality of test terminals are located at a same layer as the gate film layer or located at a same layer as the source and drain electrode film. If the film test structure as illustrated in FIG. 6 is used, the plurality of test terminals are located at the same layer as the plurality of test leads.

For example, in a case that the conductive film to be tested is the pixel electrode film, the plurality of test leads are located at a same layer as the source and drain electrode film, and the plurality of test terminals are located at a same layer as the pixel electrode film or located at a same layer as the source and drain electrode film. If the film test structure as illustrated in FIG. 6 is used, the plurality of test terminals are located at the same layer as the plurality of test leads.

The film test structure and the array substrate provided by at least one embodiment of the present disclosure have at least one of advantageous effects as follows:

(1) In the array substrate provided by at least one embodiment of the present disclosure, the film test structure applicable to the array substrate is convenient for testing square resistance, and the test accuracy is guaranteed to avoid the frequent replacement of the probes, and the consumption of the test probes is reduced, thereby the production cost is reduced.

(2) In the film test structure provided by at least one embodiment of the present disclosure, it is possible to perform a uniform test after the formation of films and the formation of the square resistance test pattern, so that it is more convenient to operate.

The following points need to be explained:

(1) The drawings of the embodiments of the present disclosure are only related to the structures related to the embodiments of the present disclosure, and other structures can refer to general designs.

(2) For clarity, in the drawings for describing the embodiments of the present disclosure, a thickness of a layer or a thickness of a region is exaggerated or reduced, that is, these drawings are not drawn according to an actual scale. It should be understood that: in a case that an element such as a layer, a film, a region or a substrate is referred to as being disposed "on" or "beneath" another element, the element may be "directly" disposed "on" or "beneath" another element, or an intermediate element may be provided.

(3) In the absence of conflict, the embodiments of the present disclosure and the features in the embodiments can be combined with each other to obtain new embodiments.

What are described above is related to the illustrative embodiments of the disclosure only and not limitative to the scope of the disclosure. Therefore, the scopes of the disclosure are defined by the accompanying claims.

The application claims priority of Chinese Patent Application No. 201620956579.3, filed on Aug. 26, 2016, the disclosure of which is incorporated herein by reference in its entirety as part of the present application.

What is claimed is:

1. A film test structure, comprising:
   a conductive film to be tested;
   a plurality of test leads arranged at a different layer from the conductive film to be tested and electrically connected with the conductive film to be tested respectively; and a plurality of test terminals electrically connected with the plurality of test leads respectively;

wherein the plurality of test terminals and the conductive film to be tested are arranged in a same layer.

2. The film test structure according to claim 1, wherein one end of each of the test leads is connected with the conductive film to be tested and the other end of the each of the test leads is connected with one of the test terminals.

3. The film test structure according to claim 2, wherein the plurality of test leads are formed integrally with the plurality of test terminals respectively.

4. The film test structure according to claim 2, wherein the test leads are disposed above or below the conductive film to be tested.

5. The film test structure according to claim 4, further comprising an insulating layer, wherein the insulating layer is disposed between the conductive film to be tested and the test terminals, the insulating layer is provided with a plurality of first via holes, and the plurality of test leads are electrically connected with the conductive film to be tested by the corresponding first via holes respectively.

6. The film test structure according to claim 5, wherein the first via holes are arranged in an intermediate region of the conductive film to be tested.

7. The film test structure according to claim 6, wherein distances between any adjacent first via holes are approximately equal.

8. The film test structure according to claim 5, wherein the plurality of first via holes are aligned in a straight line.

9. The film test structure according to claim 5, wherein a number of the first via holes is four, and the four first via holes are arranged in an equilateral quadrilateral.

10. The film test structure according to claim 5, wherein the plurality of test terminals and the conductive film to be tested are and isolated from each other, or the plurality of test terminals and the plurality of test leads are and electrically connected with each other.

11. The film test structure according to claim 10, wherein in a case that the plurality of test terminals and the conductive film to be tested are arranged in a same layer, the insulating layer is further provided with a plurality of second via holes, and the plurality of test terminals are electrically connected with the plurality of test leads by the second via holes respectively.

12. An array substrate, comprising the film test structure according to claim 1, wherein the conductive film to be tested is a gate film, a source and drain electrode film, or a pixel electrode film.

13. The array substrate according to claim 12, wherein in a case that the conductive film to be tested is the gate film, the plurality of test leads are located at a same layer as the source and drain electrode film, and the plurality of test terminals are located at a same layer as the gate film or located at a same layer as the source and drain electrode film.

14. The array substrate according to claim 12, wherein in a case that the conductive film to be tested is the source and drain electrode film, the plurality of test leads are located at a same layer as the gate film, and the plurality of test terminals are located at a same layer as the gate film layer or located at a same layer as the source and drain electrode film.

15. The array substrate according to claim 12, wherein in a case that the conductive film to be tested is the pixel electrode film, the plurality of test leads are located at a same layer as the source and drain electrode film, and the plurality of test terminals are located at a same layer as the pixel electrode film or located at a same layer as the source and drain electrode film.

16. The film test structure according to claim 3, wherein the test leads are disposed above or below the conductive film to be tested.

17. The film test structure according to claim 6, wherein the plurality of first via holes are aligned in a straight line.

18. The film test structure according to claim 7, wherein the plurality of first via holes are aligned in a straight line.

19. The film test structure according to claim 6, wherein a number of the first via holes is four, and the four first via holes are arranged in an equilateral quadrilateral.

20. The film test structure according to claim 6, wherein the plurality of test terminals and the conductive film to be tested are arranged in a same layer and isolated from each other, or the plurality of test terminals and the plurality of test leads are arranged in a same layer and electrically connected with each other.

* * * * *